(12) United States Patent
Aphek (10) Patent No.: US 10,502,679 B2
(45) Date of Patent: Dec. 10, 2019

(54) DETECTOR FOR SPECTROMETRY SYSTEM

(71) Applicant: Verifood, Ltd., Herzliya (IL)

(72) Inventor: Ori Aphek, Ramat Gan (IL)

(73) Assignee: VERIFOOD, LTD., Herzliya (IL)

( * ) Notice: Subject to any disclaimer, the term of this patent is extended or adjusted under 35 U.S.C. 154(b) by 187 days.

(21) Appl. No.: 15/727,291

(22) Filed: Oct. 6, 2017

(65) Prior Publication Data

US 2018/0031468 A1     Feb. 1, 2018

Related U.S. Application Data (63) Continuation of application No. PCT/IL2016/050362, filed on Apr. 6, 2016.

(60) Provisional application No. 62/143,976, filed on Apr. 7, 2015.

(51) Int. Cl.
    *G01N 21/25*          (2006.01)
    *H01L 27/146*       (2006.01)
              (Continued)

(52) U.S. Cl.
CPC .......... *G01N 21/255* (2013.01); *G01J 3/0272* (2013.01); *G01J 3/0289* (2013.01);
(Continued)

(58) Field of Classification Search
CPC .......... G01J 3/0272; G01J 3/2803; G01J 3/36; G01J 3/32; H01L 27/14603
See application file for complete search history.

(56) References Cited

U.S. PATENT DOCUMENTS

| 6,069,696 A | 5/2000 | McQueen et al. |
| 6,072,576 A | 6/2000 | McDonald et al. |
(Continued)

FOREIGN PATENT DOCUMENTS

| JP | H05223639 A | 8/1993 |
| WO | WO-2013065035 A1 | 5/2013 |
(Continued)

OTHER PUBLICATIONS

Fernanodo Perez "Performance of an optical encoder based on a nondiffractive beam implemented with a diffractive optical element", Aug. 7, 2015, Optical Society of America (Year: 2015).*
(Continued)

*Primary Examiner* — Maurice C Smith
(74) *Attorney, Agent, or Firm* — Wilson Sonsini Goodrich & Rosati (57) ABSTRACT

A compact spectrometer system comprising an improved detector is provided herein. The spectrometer system herein disclosed can comprises a filter, a Fourier transform optical element, and a detector. The detector can comprise a custom detector having a shape that corresponds to the pattern of light incident on the detector. The custom detector may comprise a plurality of separate detection areas, each area configured to detect a portion of the light pattern incident on the detector. The custom detector may comprise a material capable of detecting wavelengths in the short-wavelength infrared (SWIR) range. The custom detector may be configured to require a relatively low number of electrical connections such that it may be implemented using standard, low-cost electronic packaging techniques. An improved, custom detector as described herein can provide the functionality of a two-dimensional pixel array detector while being relatively simple and inexpensive to manufacture.

19 Claims, 9 Drawing Sheets

(51) Int. Cl.
*G01J 3/36* (2006.01)
*G01J 3/02* (2006.01)
*G01J 3/26* (2006.01)
*G01J 3/28* (2006.01)

(52) U.S. Cl.
CPC ............. *G01J 3/26* (2013.01); *G01J 3/2803* (2013.01); *G01J 3/36* (2013.01); *H01L 27/14603* (2013.01); *G01N 2201/0221* (2013.01)

(56) References Cited

U.S. PATENT DOCUMENTS

| | | |
|---|---|---|
| 6,333,501 B1 | 12/2001 | Labrenz |
| 6,441,375 B1 | 8/2002 | Joseph et al. |
| 6,456,373 B1 | 9/2002 | Wienecke et al. |
| 6,615,142 B1 | 9/2003 | Hovde |
| 6,639,666 B2 | 10/2003 | Li |
| 6,700,661 B1 | 3/2004 | Cadell et al. |
| 6,717,669 B2 | 4/2004 | Ruiz |
| 6,836,325 B2 | 12/2004 | Maczura et al. |
| 6,864,978 B1 | 3/2005 | Hazen et al. |
| 7,009,702 B2 | 3/2006 | Caruso et al. |
| 7,038,774 B2 | 5/2006 | Hazen et al. |
| 7,068,366 B2 | 6/2006 | Burk et al. |
| 7,075,643 B2 | 7/2006 | Holub |
| 7,084,974 B1 | 8/2006 | Barwicz et al. |
| 7,145,650 B2 | 12/2006 | Wang et al. |
| 7,151,600 B2 | 12/2006 | Imura |
| 7,158,225 B2 | 1/2007 | Tedesco et al. |
| 7,235,766 B2 | 6/2007 | Shur et al. |
| 7,238,949 B2 * | 7/2007 | Struder ............ H01L 27/14603 250/370.1 |
| 7,245,372 B2 | 7/2007 | Han |
| 7,248,370 B2 | 7/2007 | Jones |
| 7,251,037 B2 | 7/2007 | Jones |
| 7,339,665 B2 | 3/2008 | Imura |
| 7,426,446 B2 | 9/2008 | Hagler |
| 7,436,511 B2 | 10/2008 | Ruchti et al. |
| 7,489,396 B1 | 2/2009 | Vrhel et al. |
| 7,528,957 B2 | 5/2009 | Lewis et al. |
| 7,649,627 B2 | 1/2010 | Yamamoto |
| 7,697,136 B2 | 4/2010 | Imura |
| 7,767,969 B2 | 8/2010 | Nagai et al. |
| 7,817,273 B2 | 10/2010 | Bahatt et al. |
| 7,868,296 B2 | 1/2011 | Haran et al. |
| 7,876,435 B2 | 1/2011 | Becker-Ross et al. |
| 7,881,892 B2 | 2/2011 | Soyemi et al. |
| 7,907,282 B2 | 3/2011 | Coates |
| 7,929,130 B2 | 4/2011 | Dirk |
| 7,999,933 B2 | 8/2011 | McClure |
| 8,125,633 B2 | 2/2012 | Whelan et al. |
| 8,144,322 B2 | 3/2012 | Nagashima et al. |
| 8,169,607 B2 | 5/2012 | Sano et al. |
| 8,169,608 B2 | 5/2012 | Sano et al. |
| 8,247,774 B2 | 8/2012 | Chou et al. |
| 8,278,728 B2 * | 10/2012 | Murshid ............ H01L 27/1446 257/448 |
| 8,477,305 B2 | 7/2013 | Shibayama et al. |
| 8,526,002 B2 | 9/2013 | Deflores et al. |
| 8,593,628 B2 | 11/2013 | Shimbo et al. |
| 8,604,412 B2 | 12/2013 | Shibayama et al. |
| 8,654,327 B2 | 2/2014 | Bohle et al. |
| 8,675,188 B2 | 3/2014 | Liu et al. |
| 8,711,360 B2 | 4/2014 | Funamoto |
| 8,711,362 B2 | 4/2014 | Funamoto |
| 8,735,820 B2 | 5/2014 | Mertens |
| 8,742,320 B2 | 6/2014 | Shibayama et al. |
| 8,760,645 B2 | 6/2014 | Misener et al. |
| 8,773,659 B2 | 7/2014 | McClure |
| 8,786,854 B2 | 7/2014 | Miyazono |
| 8,848,187 B2 | 9/2014 | Uematsu et al. |
| 8,862,445 B2 | 10/2014 | Priore et al. |
| 8,867,033 B2 | 10/2014 | Carron et al. |
| 8,868,387 B2 | 10/2014 | Den et al. |
| 8,873,046 B2 | 10/2014 | Miyazono |
| 8,937,717 B2 | 1/2015 | Preston et al. |
| 8,976,357 B2 | 3/2015 | Uematsu et al. |
| 9,030,662 B2 | 5/2015 | Lee et al. |
| 9,063,011 B2 | 6/2015 | Chen et al. |
| 9,074,933 B2 | 7/2015 | Yokino et al. |
| 9,128,055 B2 | 9/2015 | Sekino et al. |
| 9,163,986 B2 | 10/2015 | Bouckaert |
| 9,173,508 B2 | 11/2015 | Tornwall et al. |
| 9,182,280 B1 | 11/2015 | Gardner et al. |
| 9,234,800 B2 | 1/2016 | Kawamata et al. |
| 9,239,264 B1 | 1/2016 | Demers |
| 9,297,821 B2 | 3/2016 | Walter et al. |
| 9,301,626 B2 | 4/2016 | Tornwall et al. |
| 9,310,564 B2 | 4/2016 | Martinelli et al. |
| 9,383,308 B2 | 7/2016 | Bradley et al. |
| 9,395,244 B2 | 7/2016 | Kurokawa et al. |
| 9,417,180 B2 | 8/2016 | Seo et al. |
| 9,448,165 B2 | 9/2016 | Gulati et al. |
| 9,453,794 B2 | 9/2016 | Gulati et al. |
| 9,464,934 B2 | 10/2016 | Priore et al. |
| 9,488,468 B2 | 11/2016 | Tsujii et al. |
| 9,488,523 B2 | 11/2016 | Yokino et al. |
| 9,508,765 B2 | 11/2016 | Owa et al. |
| 9,518,917 B2 | 12/2016 | Scherer et al. |
| 9,530,902 B2 * | 12/2016 | Kostamo ............ H01L 31/02005 |
| 9,546,902 B2 | 1/2017 | Kovacich et al. |
| 9,546,904 B2 | 1/2017 | Pawluczyk et al. |
| 9,557,220 B2 | 1/2017 | Yasui et al. |
| 9,568,363 B2 | 2/2017 | Yu et al. |
| 2005/0098730 A1 * | 5/2005 | Yokoi ............... H01L 27/14603 250/370.01 |
| 2005/0117151 A1 | 6/2005 | Han |
| 2005/0128477 A1 | 6/2005 | Caruso et al. |
| 2006/0132760 A1 | 6/2006 | Imura |
| 2008/0151089 A1 * | 6/2008 | Street ................ H01L 27/14601 348/308 |
| 2008/0265146 A1 | 10/2008 | Coates |
| 2008/0297791 A1 | 12/2008 | Imura |
| 2009/0051910 A1 | 2/2009 | Imura |
| 2009/0167884 A1 * | 7/2009 | Connell, Jr. ........... H04N 5/335 348/222.1 |
| 2010/0090115 A1 | 4/2010 | Lerch et al. |
| 2010/0117000 A1 | 5/2010 | Hyde et al. |
| 2010/0165337 A1 | 7/2010 | Dirk |
| 2010/0292581 A1 | 11/2010 | Howard et al. |
| 2011/0037975 A1 | 2/2011 | McClure |
| 2013/0107260 A1 | 5/2013 | Nozawa |
| 2013/0182250 A1 | 7/2013 | McClure |
| 2013/0258341 A1 | 10/2013 | Day et al. |
| 2014/0046630 A1 | 2/2014 | Smith et al. |
| 2014/0168636 A1 | 6/2014 | Funamoto et al. |
| 2014/0240711 A1 | 8/2014 | Matsushita |
| 2014/0320858 A1 | 10/2014 | Goldring et al. |
| 2014/0333932 A1 | 11/2014 | Uematsu et al. |
| 2015/0062577 A1 | 3/2015 | Hartwell et al. |
| 2015/0103354 A1 | 4/2015 | Saptari et al. |
| 2015/0108333 A1 | 4/2015 | Bouckaert |
| 2015/0116707 A1 | 4/2015 | Tatsuda |
| 2015/0119661 A1 | 4/2015 | Gilbert et al. |
| 2015/0153225 A1 | 6/2015 | Baudelet |
| 2015/0323383 A1 | 11/2015 | Pastore et al. |
| 2016/0018260 A1 | 1/2016 | Samuels |
| 2016/0091369 A1 | 3/2016 | Sakurai et al. |
| 2016/0103069 A1 | 4/2016 | Umapathy et al. |
| 2016/0223400 A1 | 8/2016 | Carron et al. |
| 2016/0231171 A1 | 8/2016 | Assefa et al. |
| 2016/0245700 A1 | 8/2016 | Uematsu et al. |
| 2016/0258813 A1 | 9/2016 | Kuri |
| 2016/0263910 A1 | 9/2016 | Kanai et al. |
| 2016/0282182 A1 | 9/2016 | Kanai et al. |
| 2016/0299004 A1 | 10/2016 | Thamm |
| 2016/0305820 A1 | 10/2016 | Zollars et al. |
| 2016/0313184 A1 | 10/2016 | Owechko |
| 2016/0334274 A1 | 11/2016 | Xu |
| 2016/0356646 A1 | 12/2016 | Wiegand et al. |
| 2016/0356647 A1 | 12/2016 | Wiegand et al. |
| 2016/0356704 A1 | 12/2016 | Kim et al. |

(56) References Cited

U.S. PATENT DOCUMENTS

| 2017/0003167 A1 | 1/2017 | Ave |
| 2017/0027447 A1 | 2/2017 | Sutin et al. |
| 2017/0038257 A1 | 2/2017 | Liu et al. |

FOREIGN PATENT DOCUMENTS

| WO | WO-2013082272 A1 | 6/2013 |
| WO | WO-2013106307 A1 | 7/2013 |
| WO | WO-2013148461 A1 | 10/2013 |
| WO | WO-2013150290 A1 | 10/2013 |
| WO | WO-2013162850 A1 | 10/2013 |
| WO | WO-2013163268 A1 | 10/2013 |
| WO | WO-2013165887 A1 | 11/2013 |
| WO | WO-2014014534 A2 | 1/2014 |
| WO | WO-2014033783 A1 | 3/2014 |
| WO | WO-2014014534 A3 | 4/2014 |
| WO | WO-2014064447 A1 | 5/2014 |
| WO | WO-2014102629 A1 | 7/2014 |
| WO | WO-2014129305 A1 | 8/2014 |
| WO | WO-2014139003 A1 | 9/2014 |
| WO | WO-2014192007 A1 | 12/2014 |
| WO | WO-2015009602 A1 | 1/2015 |
| WO | WO-2015015493 A2 | 2/2015 |
| WO | WO-2015015493 A3 | 3/2015 |
| WO | WO-2015038372 A1 | 3/2015 |
| WO | WO-2015042617 A1 | 3/2015 |
| WO | WO-2015058166 A2 | 4/2015 |
| WO | WO-2015058166 A3 | 6/2015 |
| WO | WO-2015101992 A2 | 7/2015 |
| WO | WO-2015101992 A3 | 9/2015 |
| WO | WO-2015138028 A2 | 9/2015 |
| WO | WO-2015138028 A3 | 11/2015 |
| WO | WO-2016022283 A1 | 2/2016 |
| WO | WO-2016033224 A1 | 3/2016 |
| WO | WO-2016059946 A1 | 4/2016 |
| WO | WO-2016124659 A1 | 8/2016 |
| WO | WO-2016125164 A2 | 8/2016 |
| WO | WO-2016125165 A2 | 8/2016 |
| WO | WO-2016162865 A1 | 10/2016 |
| WO | WO-2016125165 A3 | 12/2016 |
| WO | WO-2016196727 A2 | 12/2016 |
| WO | WO-2016125164 A3 | 1/2017 |
| WO | WO-2016196727 A3 | 1/2017 |

OTHER PUBLICATIONS

Ozlem Senlik, "Concentric Multipixel Silicon Photodiode Array Probes for Spatially Resolved Diffuse Reflectance Spectroscopy", Dec. 5, 2015, IEEE Journal of Selected Topics in Quantum Electronics, vol. 22 (Year: 2015).*

Ettenberg, et al., Indium galllium arsenide handles broad task spectrum in near infrared, Laser Focus World, Available at http://www.laserfocusworld.com/articles/print/volume-38/issue 8/features/detectors/indium-gallium-arsenide-hand les-broad-task-spectrum-in-near-infrared.html>, Accessed on Aug. 1, 2002.

International search report and written opinion dated Oct. 13, 2016 for PCT Application IL-2016050362.

U.S. Appl. No. 61/861,893, filed Aug. 21, 2013.

U.S. Appl. No. 61/985,447, filed Apr. 28, 2014.

* cited by examiner

DETECTOR FOR SPECTROMETRY SYSTEM

CROSS-REFERENCE

The present application is a continuation of International Patent Application No. PCT/IL2016/050362, filed on Apr. 6, 2016, entitled "DETECTOR FOR SPECTROMETRY SYSTEM", which claims the benefit of U.S. Provisional Application Ser. No. 62/143,976, filed on Apr. 7, 2015, entitled "Detector for Spectrometry System", the entire disclosures of which are incorporated herein by reference.

The subject matter of the present application is related to PCT Application PCT/IL2012/000367, filed Oct. 31, 2012, entitled "Low-Cost Spectrometry System for End-User Food Analysis", PCT Application PCT/IL2014/050688, filed on Jul. 30, 2014, entitled "Spectrometry System and Method, Spectroscopic Devices and Systems", PCT Application PCT/IL2015/050002, filed on Jan. 1, 2015, entitled "Spectroscopic Devices and Systems", PCT Application PCT/IL2016/050130, filed on Feb. 4, 2016, entitled "Spectrometry System with Visible Aiming Beam", and PCT Application PCT/IL2016/050129, filed on Feb. 4, 2016, entitled "Embedded Applications for Spectrometry System", each of which is incorporated herein by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Spectrometers are used for many purposes. For example, spectrometers are used in the detection of defects in industrial processes, satellite imaging, and laboratory research. However, these instruments have typically been too large and too costly for the consumer market.

Spectrometers detect radiation from a sample and process the resulting signal to obtain and present information about the sample that includes spectral, physical and chemical information about the sample. These instruments generally include some type of spectrally selective element to separate wavelengths of radiation received from the sample, and a first-stage optic, such as a lens, to focus or concentrate the radiation onto an imaging array.

The prior spectrometers can be less than ideal in at least some respects. Prior spectrometers having high resolution can be larger than ideal for use in many portable applications. Although prior spectrometers with decreased size have been proposed, the prior spectrometers having decreased size and optical path length can have less than ideal resolution, sensitivity and less accuracy than would be ideal. Detectors used in prior spectrometers can have detectable wavelength ranges that are less than ideal. Also, the cost of prior spectrometers can be greater than would be ideal. The prior spectrometers can be somewhat bulky, difficult to transport and the optics can require more alignment than would be ideal in at least some instances. Because of their size and cost, prior spectrometers can be difficult to integrate into other consumer appliances or devices in which a spectrometer may be useful.

The prior spectrometers may rely on detectors that are less than ideal. Prior spectrometers can rely on arrays such as CCD arrays, which are less than ideally suited to detect a light pattern incident on the array. The prior arrays can results in a greater number of element and electrical connections than would be ideal, and can increase one or more of the size, weight, or complexity of the spectrometer.

For many materials, the fundamental absorption peaks are in the mid-wavelength infrared (MWIR) to long-wavelength infrared (LWIR) range, for example about 3 to about 12 µm. Prior spectrometers configured to measure light in this range can be complex, large and expensive, due to the high cost of light sources, detectors and optics for this wavelength band. Although lower-cost, smaller spectrometers may work in shorter wavelength ranges, the results can be less than ideal.

The prior detectors for measuring light can be less than ideally suited for use with spectrometers. For example, prior spectrometers using infrared detectors may use detectors that are more complicated and expensive than would be ideal. Also, prior detectors may have pixels sizes and shapes that are less than ideally suited for use with spectrometers.

In light of the above, an improved spectrometer and interpretation of spectral data that overcomes at least some of the above mentioned deficiencies of the prior spectrometers would be beneficial. Ideally, such a spectrometer would be compact, integrated with appliances, sufficiently rugged and low in cost to be practical for end-user spectroscopic measurements of items, and convenient to use. Further, it would be helpful to provide an improved detector for a compact spectrometer, the detector having high sensitivity to a wide range of wavelengths.

SUMMARY OF THE INVENTION

An improved compact spectrometer system comprising an improved detector is disclosed herein. The spectrometer system comprises optics and a detector. The optics may comprise one or more of a filter, a Fourier transform optical element, or a detector. The detector may comprise detector elements having a shape that corresponds to the shape profile of the pattern of light incident on the detector. The optics of the spectrometer can be configured to provide an optical signal varying along one or more dimensions in response to the spectra and substantially invariant along another dimension. The optics can be configured to provide a rotationally symmetric optical signal, and the detector can comprise rotationally symmetric elements. The optics can be configured to provide an optical signal having an annular shape profile distribution, and the detector elements may comprise annular shapes corresponding to the annular shape profile of the optical signal. The detector may comprise a plurality of separate detection elements extending over areas, each element area shaped to detect a portion of the light pattern incident on the detector. The optics may comprise an array of optical elements, and the detector may comprise an array of detector elements corresponding to the array of optical elements. The detector may comprise an array of similarly shaped detector elements, such as an array of arcuate detector elements. Each of the arcuate detector elements may comprise a generally curved shape profile extending along a plane of the detector, such as an annular shape profile, or ring segments. The arcuate detector elements can be arranged concentrically, such that each arc corresponds to a center in common with or in close proximity to a center of another arcuate detector element. The detector may comprise a material capable of detecting wavelengths, such as wavelengths in the short-wavelength infrared (SWIR) range. The detector may be configured with a relatively low number of electrical connections implemented with standard, low-cost electronic packaging techniques, thereby decreasing the size, weight and complexity of the spectrometer. An improved, custom detector as described herein can provide the functionality of a two-dimensional pixel array detector while being relatively simple and inexpensive to manufacture, with decreased circuitry and decreased size and weight.

In one aspect, disclosed herein is a detector to measure spectra of a sample. The detector comprises a plurality of arcuate photo sensor elements, and circuitry coupled to the plurality of arcuate photo sensor elements to measure an amount of light incident on each of the plurality of arcuate photo sensor elements.

The plurality of arcuate photo sensor elements may comprise a plurality of concentric photo sensor elements. Each of the plurality of arcuate photo sensor elements may comprise a circumferential shape profile corresponding to a center of curvature concentric with other arcuate photo sensor elements of the plurality. The plurality of arcuate photo sensor elements may comprise a plurality of ring segments. The plurality of arcuate photo sensor elements may comprise a plurality of annular elements extending around a central photo sensor element. The plurality of arcuate photo sensor elements may comprise a plurality of annular elements, each annular element extending at least partially around a central circular photo sensor element. The plurality of arcuate photo sensor elements may comprise a plurality of annular sensor elements, each annular sensor element comprising a radial thickness, wherein the thickness of the plurality of annular elements decreases progressively for said each annular element away from a common center of the plurality of annular photo sensor elements.

The plurality of arcuate photo sensor elements may be collectively configured to sense light having a wavelength within a short-wavelength infrared range. The plurality of arcuate photo sensor elements may be collectively configured to sense light having a wavelength greater than about 1 μm.

Each of the plurality of arcuate photo sensor elements may be configured to be measured separately using a separate electrical connection. The detector may further comprise a plurality of anode bonds coupling each of the plurality of arcuate photo sensor elements with the circuitry, and a single common cathode bond coupling the plurality of arcuate photo sensor elements with the circuitry. The detector may further comprise a plurality of cathode bonds coupling each of the plurality of arcuate photo sensor elements with the circuitry, and a single common anode bond coupling the plurality of arcuate photo sensor elements with the circuitry.

The plurality of arcuate photo sensor elements may define a clearing. The detector may further comprise electrical wires to couple the plurality of arcuate photo sensor elements to the circuitry, wherein the electrical wires may be coupled to the plurality of the arcuate photo sensor elements at the clearing.

Each of the plurality of arcuate photo sensor elements may comprise a plurality of segments, wherein each of the plurality of segments may be configured to be measured separately using a separate electrical connection.

The plurality of arcuate photo sensor elements may comprise one or more of silicon PIN, lattice matched indium gallium arsenide (InGaAs), strained InGaAs, mercury cadmium telluride (MCT), superlattice, lead(II) sulfide (PbS), geranium (Ge), indium antimonide (InSb), lead(II) selenide (PbSe), photovoltaic MCT (PV MCT), indium arsenide (InAs), or other infrared semiconductors.

In another aspect, disclosed herein is a spectrometer comprising optics configured to receive input light and generate output light having an arcuate optical pattern. The spectrometer further comprises a detector configured to receive the output light having the arcuate optical pattern, the detector comprising a plurality of sensor elements shaped to correspond to the arcuate optical pattern.

The arcuate optical pattern may comprise a rotationally symmetric optical pattern, wherein the output light varies with radius in response to wavelengths of the input light. The arcuate optical pattern may comprise a plurality of portions corresponding to a plurality of wavelength bands of the input light, and wherein each of the plurality of sensor elements is configured to receive light having a wavelength band of the plurality of wavelength bands. The plurality of sensor elements may comprise a plurality of concentric rings or ring segments. The plurality of rings or ring segments may have spacing and width corresponding to the arcuate optical pattern generated by the optics.

The optics may comprise one or more of an optical filter, an optical lens, or a Fourier transform focusing element. The plurality of sensor elements comprises a plurality of arcuate photo sensor elements.

The detector may further comprise circuitry coupled to the plurality of sensor elements to measure an amount of light incident on each of the plurality of sensor elements.

The optics may comprise an array of optical filters and an array of optical lenses, and the detector may comprise an array of detectors. Each detector of the array of detectors may comprise a plurality of sensor elements shaped to correspond to the arcuate optical pattern.

In another aspect, disclosed herein is a method comprising providing a spectrometer comprising optics and a detector, wherein the detector comprises a plurality of sensor elements shaped to correspond to an arcuate optical pattern of the input light transmitted through the optics. The method further comprises measuring an amount of light incident on each of the plurality of sensor elements, and determining the spectra of the input light based on measurement data generated by the plurality of sensor elements.

Each of the plurality of sensor elements may comprise a plurality of segments. The method may comprise measuring an amount of light incident on each segment of the plurality of segments using a separate electrical connection, and summing measurements from the plurality of segments.

In another aspect, disclosed herein is a method of manufacturing a detector as disclosed herein, the method comprising patterning the plurality of sensor elements using photolithography.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

A better understanding of the features and advantages of the present disclosure will be obtained by reference to the following detailed description that sets forth illustrative embodiments, in which the principles of embodiments of the present disclosure are utilized, and the accompanying drawings.

As used herein the term arcuate encompasses one or more of curved, elliptical, annular or conical shapes, and portions of these shapes and linear approximations thereof.

As used herein, like characters refer to like elements.

As used herein, the term "light" encompasses electromagnetic radiation having wavelengths in one or more of the ultraviolet, visible, or infrared portions of the electromagnetic spectrum.

As used herein, the term "dispersive" is used, with respect to optical components, to describe a component that is designed to separate spatially, the different wavelength components of a polychromatic beam of light. Non-limiting examples of "dispersive" optical elements by this definition include diffraction gratings and prisms. The term specifically excludes elements such as lenses that disperse light because of non-idealities such as chromatic aberration or elements such as interference filters that have different transmission profiles according to the angle of incident radiation. The term also excludes the filters and filter matrixes described herein.

The spectrometer and detector as disclosed herein are well suited for combination with many prior art spectrometer components. The detector can be used with spectrometers providing an optical signal that varies along one dimension and remains substantially fixed along another dimension in response to the wavelengths of light. The optical signal may comprise an arcuate optical pattern, wherein the optics of the spectrometer may receive input light from a sample and transmit output light having the arcuate optical pattern. For example, the optical signal may comprise an rotationally symmetric optical signal, in which light varies with radius and remains substantially fixed circumferentially around the radius in response to the wavelengths of light of the spectra. The detector may comprise sensor elements having corresponding shapes, such as arcuate detector elements corresponding to an arcuate optical pattern of light incident on the detector, or annular detector elements corresponding to an annular shape profile distribution of the rotationally symmetric optical signal, for example. The detector elements can be shaped to correspond to the optical signal in one or more of many ways, such as one or more of arcuate, annular, circular, elliptical, or linear. The detector may comprise an array of shaped elements such as an array of arcuate or annular elements.

Figure 1:
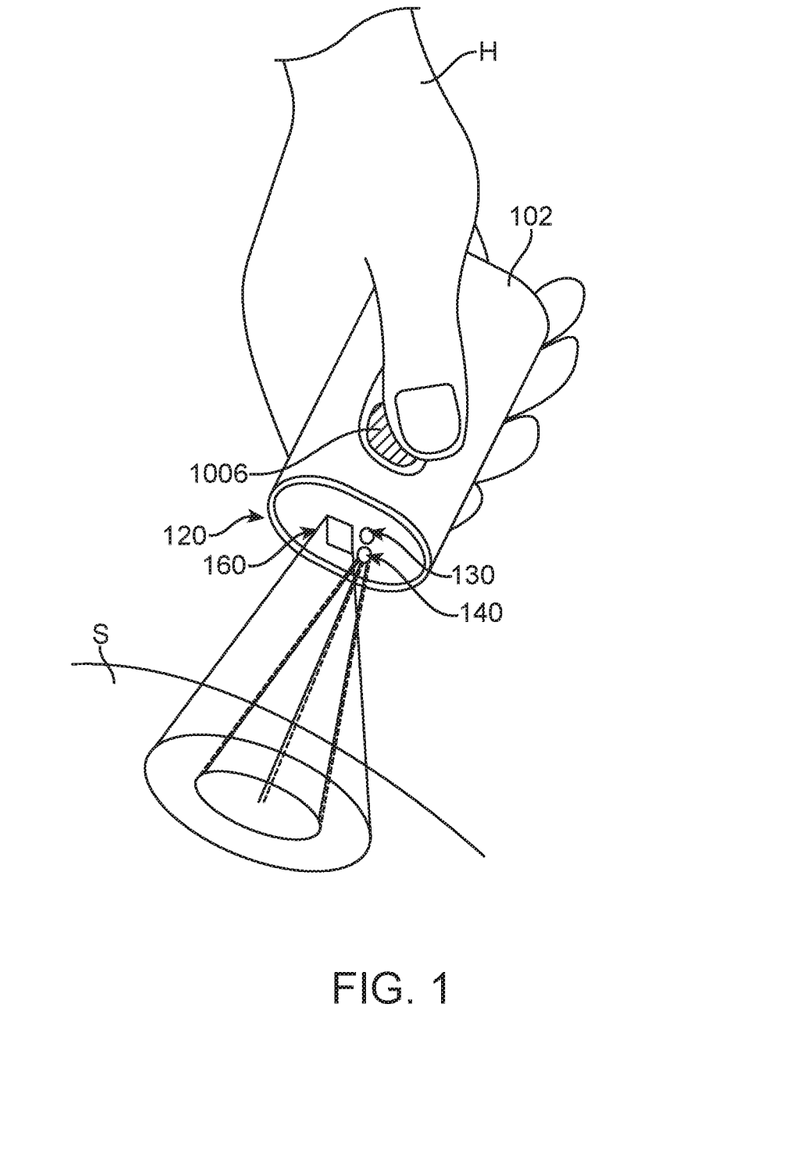
FIG. 1 shows an isometric view of an exemplary compact spectrometer.

FIG. 1 shows an isometric view of a compact spectrometer 102, in accordance with configurations. The spectrometer 102 can be used as a general purpose material analyzer for many applications. In particular, the spectrometer 102 can be used to identify materials or objects, provide information regarding certain properties of the identified materials, and accordingly provide users with actionable insights regarding the identified materials. The spectrometer 102 comprises a spectrometer head 120 configured to be directed towards a sample material S. The spectrometer head 120 comprises a spectrometer module 160, configured to obtain spectral information associated with the sample material S. The spectrometer head 120 may comprise an illumination module 140, comprise a light source configured to direct an optical beam to the sample material S within the field of view of the detector. The spectrometer head 120 may further comprise a sensor module 130, which may, for example, comprise a temperature sensor. The spectrometer may comprise simple means for users to control the operation of the spectrometer, such as operating button 1006. The compact size of the spectrometer 102 can provide a hand held device that can be directed (e.g., pointed) at a material to rapidly obtain information about the material. For example, as shown in FIG. 1, the spectrometer 102 may be sized to fit inside the hand H of a user.

For many materials, the fundamental absorption peaks are in the mid-wavelength infrared (MWIR) to long-wavelength infrared (LWIR) range, for example about 3 to about 12 μm. The detector disclosed herein can be configured to measure wavelengths in the about 3 to about 12 μm range. Alternatively or in combination, the detector can be configured to use absorption peaks in overtones expressed in shorter wavelengths than the fundamental absorption peaks Reference is now made to FIG. 2A, which illustrates one non-limiting example of the compact spectrometer 102 suitable for use with a detector as disclosed herein. The spectrometer comprises an optical filter 200, a first Fourier transform focusing element 201, and a detector 204. The first Fourier transform focusing element 201 may be a plano-convex lens oriented such that the convex side is facing the optical filter. The detector is located in a predetermined plane $P_1$, which may be the focal plane of the first Fourier transform focusing element.

Optical filter 200 can be of any type known in the art. Non-limiting examples of suitable optical filters include Fabry-Perot (FP) resonators, cascaded FP resonators, and interference filters. In a typical embodiment of the simplest possible arrangement shown in FIG. 2A, a narrow bandpass filter ($\leq 10$ cm$^{-1}$) with a wide blocking range outside of the transmission band (at least 200 nm) can be used. The center wavelength (CWL) of the filter may vary with the incident angle of the light impinging upon it.

Figure 2A:
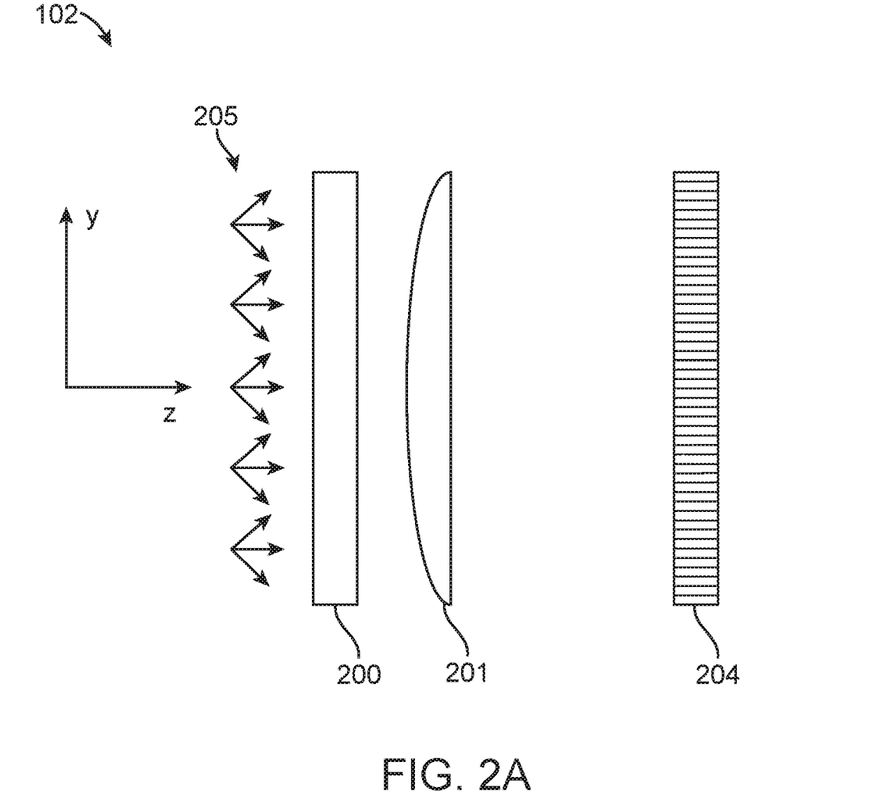
FIG. 2A shows a schematic diagram of an exemplary optical layout for a compact spectrometer.

Detector 204 may be of any suitable type known in the art capable of detecting light in the wavelength range of interest; the compact spectrometer system disclosed herein can be used from the UV to the IR, depending on the nature of the spectrum being obtained and the particular spectral properties of the sample being tested. Because the spectra can be obtained by measuring the intensity of light as a function of the position in a predetermined plane (e.g. the focal plane of the first Fourier transform focusing element), a detector that is capable of measuring intensity as a function of position (e.g. an array detector or a two-dimensional image sensor) may be used.

The basic principle of operation of compact spectrometer 102 is as follows. Light 205 impinges upon optical filter 200. Assuming that light 205 is approximately spatially invariant over the area of the optical filter (in typical embodiments of the invention, the entrance aperture has an area of the order of 1 mm$^2$), and that the light impinges upon the filter at a sufficiently wide range of propagation angles, both of which are reasonable assumptions, the light passing through the filter is angularly encoded after passing through the optical filter. The Fourier transform focusing element 201 performs (approximately) a spatial Fourier transform of the angle-encoded light, transforming it into a spatially-encoded spectrum. That is, the intensity of light recorded by the detector 204 as a function of position (pixel number) on the detector is correlated to the intensity at wavelength of the light corresponding to that position.

Figure 2B:
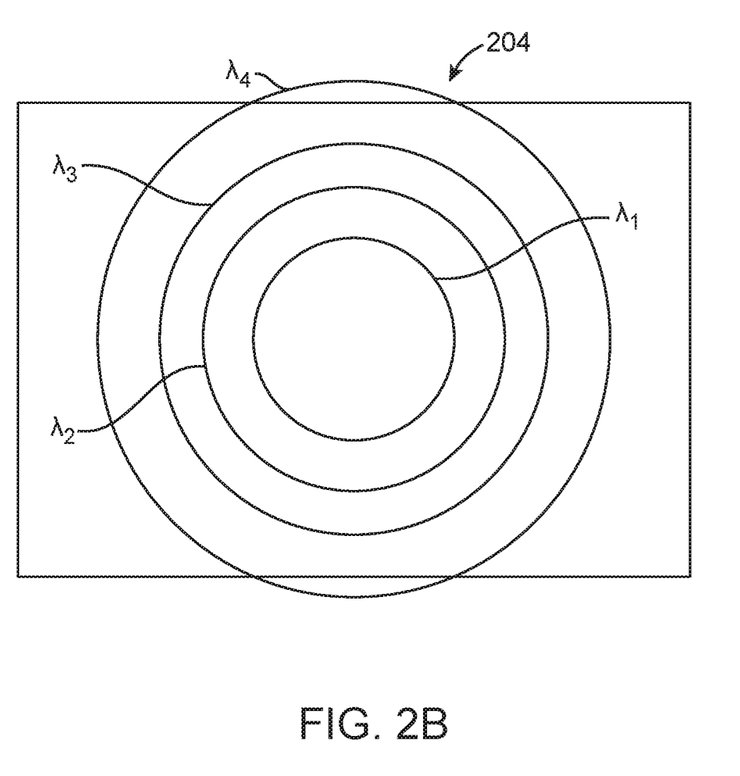
FIG. 2B presents a schematic illustration of the dispersion of light upon a detector according to one configuration of a compact spectrometer.

Reference is now made to FIG. 2B, which illustrates the dispersion of light on detector 204 for an embodiment in which the detector is a 2-D image sensor located in plane $P_1$ which is substantially coincident with the focal plane of first Fourier transform focusing element 201, and the first Fourier transform focusing element is a lens with radial symmetry. As can be seen in the figure, light of different wavelengths ($\lambda_1$, $\lambda_2$, $\lambda_3$, $\lambda_4$, etc.) can arrive at the detector as a series of circles of different radii proportional to the wavelength. The relationship between the wavelength and the radius of the corresponding circle may not be linear.

The light pattern projected on the sensor plane may have circular symmetry, wherein the distance of each pixel from the center correlates to the wavelength of the incident light. The sensor can capture an image that holds the information for separating the spectrum of the incident light. A calibration procedure and algorithm can identify a conversion function from a pixel location to wavelength, and the derived calibration parameters can be attached to each spectrometer device. When a spectrum is measured, the pixels which correspond to the same wavelength can be summed, as they represent the signal generated from the same wavelength. The summation may be a more complicated mathematical formula than a simple sum, taking into account different calibration issues. The spectrometer output for the value of the intensity of light per single wavelength can be generated from light intensity measurements of many pixels (typically thousands) of the two dimensional sensor array.

The configuration illustrated in FIGS. 2A and 2B may be used in a longer wavelength range as well, to gain from the lower order overtones of the absorption peaks. The absorption peaks in the short-wavelength infrared (SWIR) range, for example, are in some cases much more pronounced than the absorption peaks in NIR. SWIR is usually defined by the wavelength range from about 1.0 um to about 2.5 um.

The configuration of FIGS. 2A and 2B can be extended to an array of lenses and a corresponding array of detectors as disclosed herein. Examples of spectrometers suitable for use in combination with the present spectrometer are described in WO/2015/015493, claiming priority to the following US provisional applications, which are fully incorporated herein by reference:

| | | |
|---|---|---|
| 61/861,893 | 2 Aug. 2013 | US |
| 61/923,422 | 3 Jan. 2014 | US |
| 61/985,447 | 28 Apr. 2014 | US |

The spectrometer may comprise a plurality of optical channels, and each channel may have a detector as disclosed herein comprising a plurality of annular detector elements.

Figure 3:
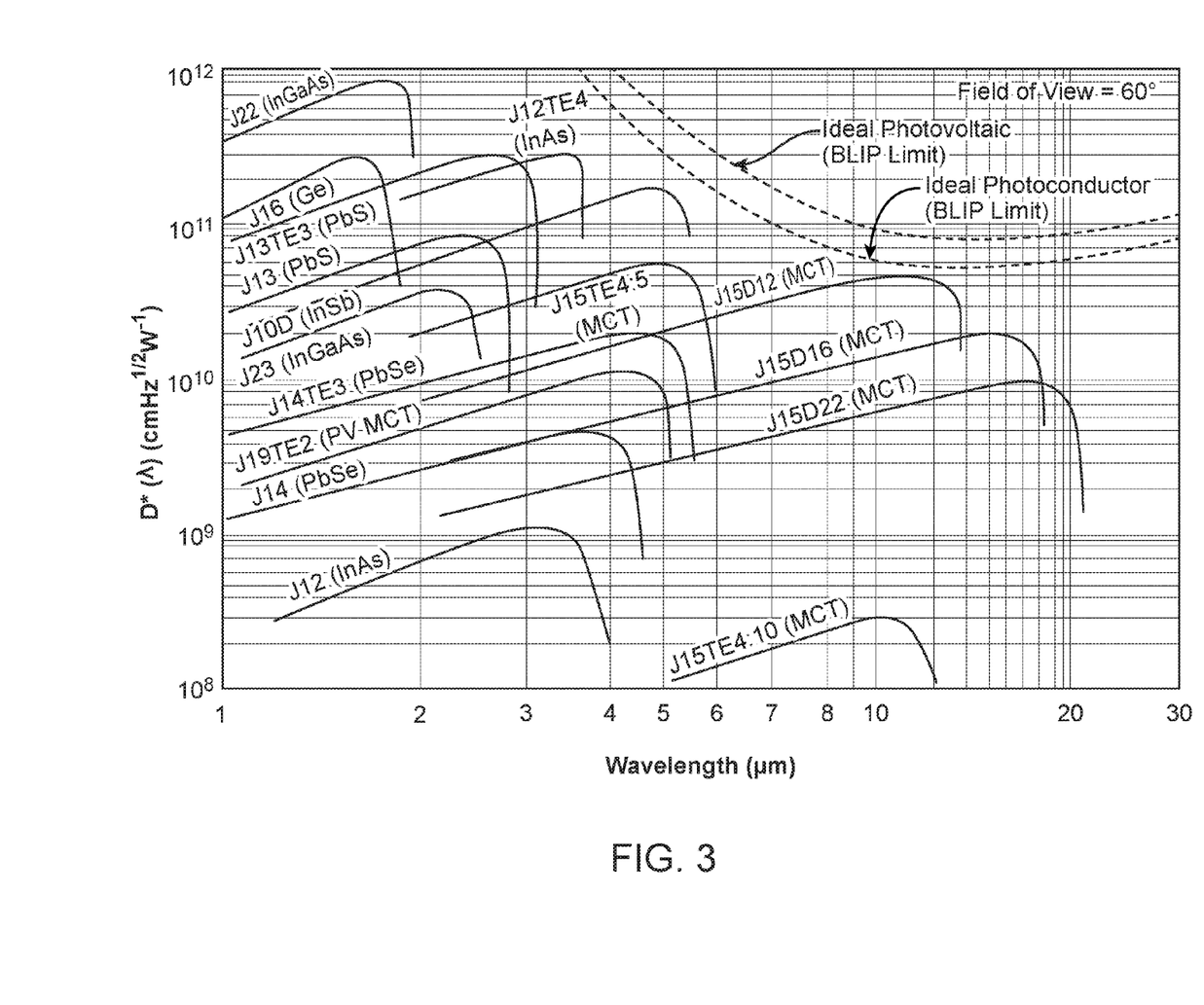
FIGS. 3 and 4 show examples of detectors that may be used in the SWIR range.
Figure 4:
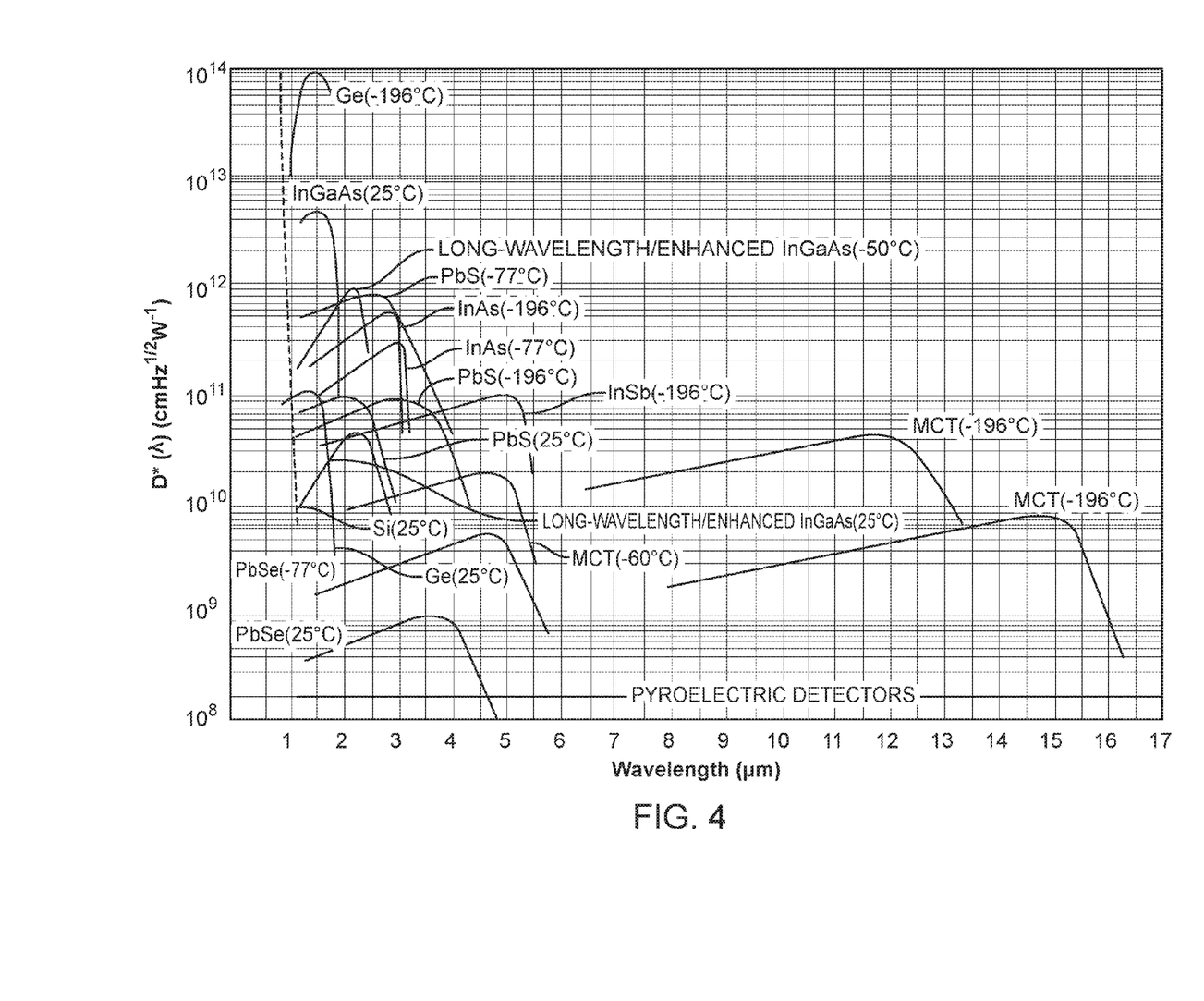

FIGS. 3 and 4 show examples of detectors materials that may be used in the SWIR range. FIG. 4 also shows silicon detectors, indicated with the dashed line on the left. Some commonly used detectors that are configured to work in the SWIR range include Lattice-Matched Indium Gallium Arsenide (InGaAs) detectors, which are low-noise uncooled detectors that work in the sub-wavelength band of SWIR up to about 1.7 um. Other detectors such as strained InGaAs, Mercury Cadmium Telluride (MCT), lead(II) sulfide (PbS), geranium (Ge), indium antimonide (InSb), lead(II) selenide (Pb Se), photovoltaic MCT (PV MCT), and indium arsenide (InAs) detectors are usually capable of detecting light up to 2.5 um, covering the entire SWIR range (Extended SWIR), as shown in FIGS. 3 and 4. However, these detectors can have higher noise than Lattice Matched InGaAs detectors by several orders of magnitude.

Figure 5A:
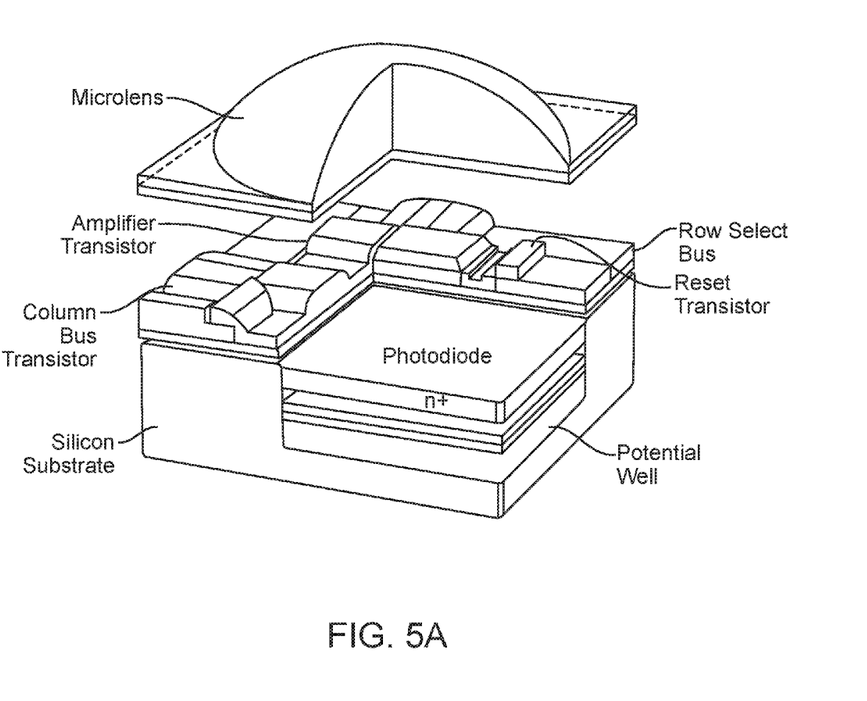
FIG. 5A shows an example of a single-pixel SWIR detector having components suitable for incorporation in accordance with examples disclosed herein.
Figure 5B:
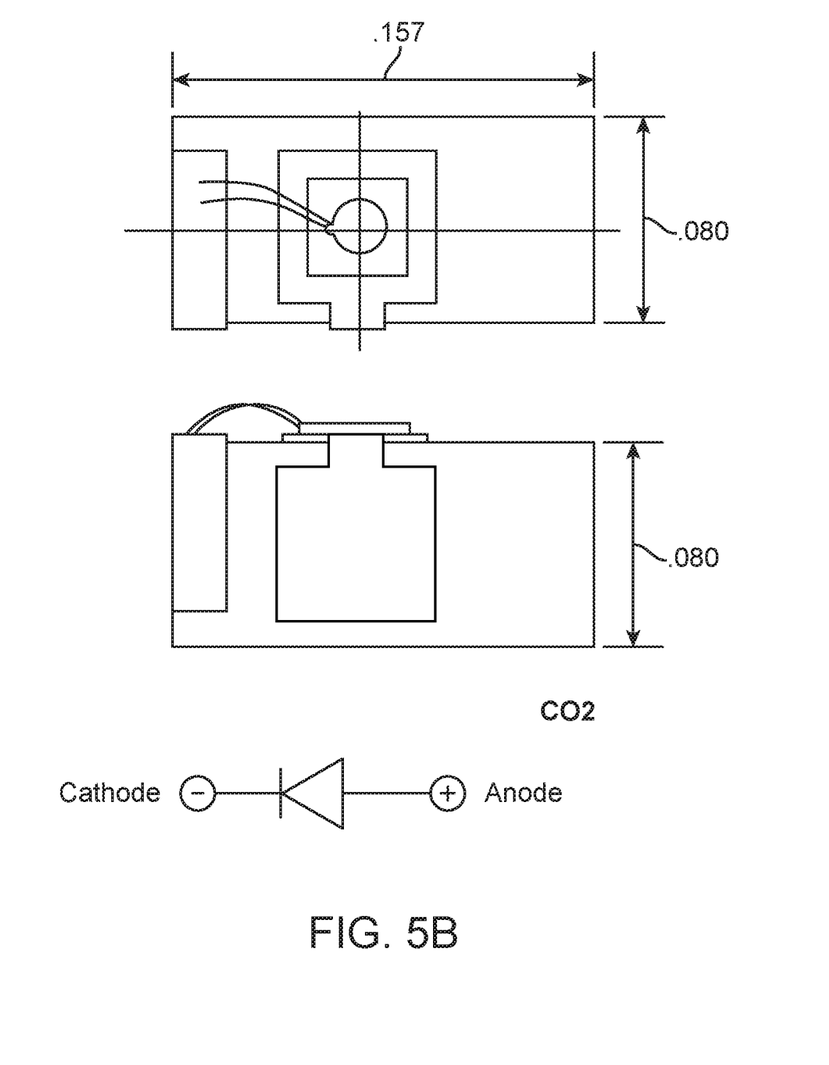
FIG. 5B shows top and side views of a single-pixel SWIR detector wire-bonded to a driver having components suitable for incorporation in accordance with examples disclosed herein.

FIG. 5A shows an example of a single-pixel SWIR detector and circuitry suitable for incorporation in accordance with examples disclosed herein. This is a single design of an InGaAs PIN-diode, wire bonded to a low noise driver. FIG. 5B shows top and side views of such a detector wire-bonded to a driver and corresponding circuitry. Single-pixel or small linear array InGaAs detectors are often used in many industries such as fiber optic communications. Such a technology can be easier to implement than two-dimensional InGaAs PIN-diode arrays, since there is no need for the complex and unique flip-chip bonding technique. For a single PIN-diode, the electronics (e.g., amplifier, bus, etc.) can be monolithically integrated with the diode, with two wire bonding connections usually sufficient, as shown in FIG. 5B. Also, the area of the InGaAs layer used may be smaller, and standard packaging technologies can be used. Accordingly, single-pixel IngGaAs PIN diodes can be relatively inexpensive; for example, a TO-can packaged, 2 mm-diameter lattice-matched InGaAs detector can be as low as about $20 in large quantities, and lower-priced without the package.

A custom detector may be provided to combine the functionality of a two-dimensional array detector and the simplicity and lower cost of a single-pixel detector. Such a detector may be useful when a low-cost two-dimensional pixel array detector or camera is not available, for example when the wavelength band of the light to be measured is beyond the sensitivity of a typical silicon detector (e.g., above 1 um), or when high sensitivity is required.

The custom detector may comprise light detection elements or areas that are shaped in a way that corresponds to the pattern of light generated by a given wavelength. For example, if each wavelength generates a ring-shaped light on the focal plane, then the pixels may be shaped as rings, or as parts of rings (to conform to constraints that will be further described). For example, if the detector is configured to measure ten wavelength bands, the detector may comprise ten concentric annularly shaped rings, the rings having spacing and width corresponding to the pattern generated by the optical filter and the Fourier optics. The custom detector may further comprise anode bonds for each light detection element and a single, common cathode bond for all light detection elements; alternatively, the detector may comprise cathode bonds for each light detection element and a single, common anode bond for all light detection elements. For example, in an exemplary custom detector configured to measure ten wavelength bands, the detector may comprise 10 anode bonds and a single cathode bond, or 10 cathode bonds and a single anode bond. Such low-count bonding requirements can be implemented using standard low-cost electronic packages and packaging techniques, such as wire bonding, or low-cost large-pitch (~100 um) flip-chip bonding.

Such a custom detector may be manufactured, for example, by patterning the shape of the detectors in the mask-set used in the FAB manufacturing of an InGaAs detector. The entire manufacturing process may be identical to the process used when manufacturing InGaAs PIN diodes. A custom detector as described herein can provide the functionality of a two-dimensional pixel array camera, using custom detectors which may be only slightly more complex and expensive than a single-pixel PIN photodiode.

Figure 6:
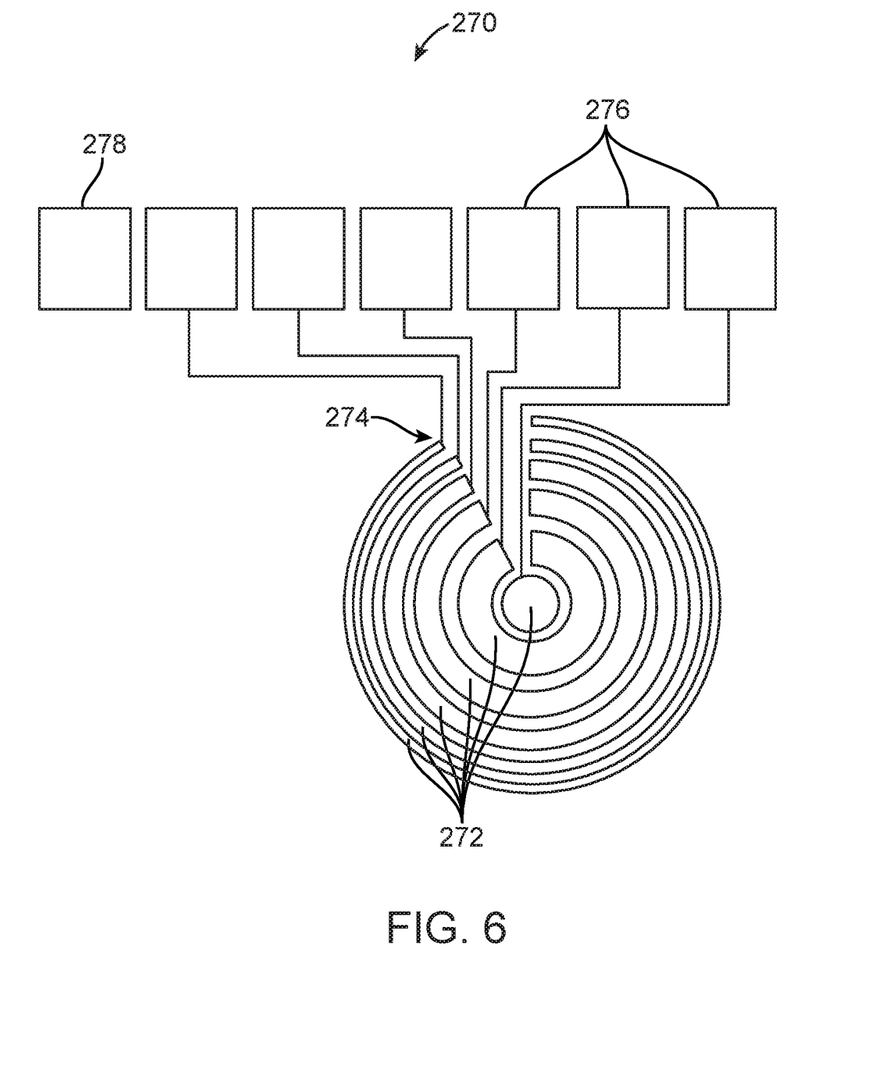
FIG. 6 illustrates an exemplary custom detector that may be used in the SWIR range.

FIG. 6 illustrates an exemplary custom detector 270 that may be used in the SWIR range. The exemplary custom detector 270 comprises a plurality of six electrically separated detection areas 272. The central detection area is circular, while the others comprise annuli comprising concentric ring-shapes. The detector may comprise an optional clearing 274 in order to allow connectivity to the wire bonding pads, so that the length and height of the wire bond wires may be reduced. The anode of each detection area may be connected to a separate bonding pad 276, while the common cathode may be connected to a separate pad 278. The dimensions and shapes of the separate detection areas can correspond to the dimensions and shapes of the pattern of light incident on the detector, such as the pattern shown in FIG. 2B. Additional aspects may also be accounted for in determining the dimensions and shapes of the detection areas, such as spectral resolution, alignment errors, and the like.

To mitigate the effect of alignment errors, each ring may be split into several (for example 3 or 4) segments, each segment connected to a separate pad and measured separately. In such a configuration, if the detector is not perfectly aligned, portions of different rings can be summed to compensate for the misalignment. Such a configuration may be particularly useful for the outer rings, which can tend to be thinner and thus more susceptible to being affected by misalignment errors.

The number of detection areas may be increased to several tens, and in some cases several hundreds. The number of detection areas may be limited by the interconnect technology used and the area necessary for supporting the interconnection elements, in contrast to cameras which may comprise several megapixels. The detection areas can be patterned using photolithography techniques. The detector may comprise a plurality of concentric array detectors. A detector as described herein may be manufactured using the same or similar processes as for the fabrication for a single photodiode as described herein. The detector may comprise silicon PIN (to achieve enhanced sensitivity within the NIR spectrum), lattice matched InGaAs, strained InGaAs, MCT, superlattice, PbS, InAs, or many other infrared semiconductors. Noise level may be an important aspect to consider in selecting the detector material: lattice matched InGaAs generally has the lowest noise level among detectors capable of sensing wavelengths above 1 um. As the cutoff wavelength increases, noise generally increases, and cooling may be needed to obtain usable measurements of a spectrum, which can lead to higher costs. Noise level requirements may be calculated for each specific application, and an appropriate detector material may be selected to satisfy the calculated requirements.

Figure 7:
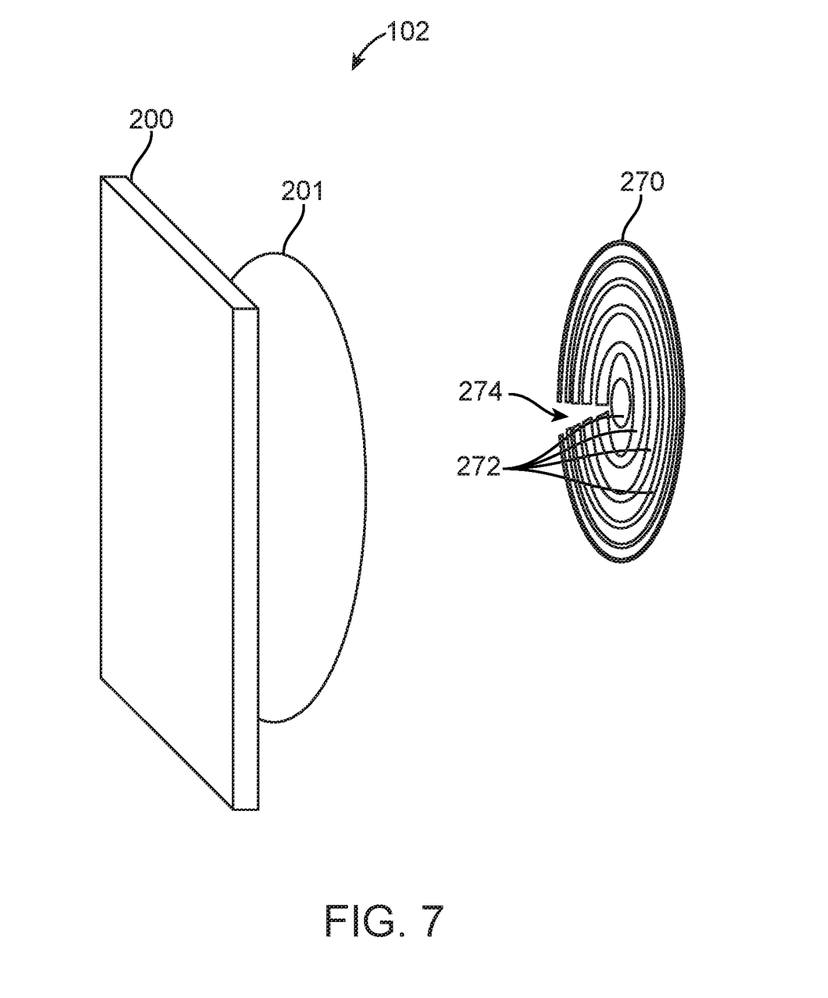
FIG. 7 illustrates an exemplary configuration of a compact spectrometer comprising a custom detector as in FIG. 6.

FIG. 7 illustrates an exemplary configuration of the compact spectrometer 102 comprising a custom detector 270. The spectrometer may further comprise one or more of an optical filter 200 or Fourier optics 201, similarly to the spectrometer described in FIG. 2A. The custom detector 270 may comprise a lower pixel count than a two-dimensional pixel array detector such as detector 204 described in relation to FIG. 2A. As described herein, the pixels or detection areas 272 of the custom detector 270 can be arranged as concentric rings or concentric segmented rings, which correspond to the spectral pattern generated by the filter 200 and Fourier optics 201.

The spectrometer can be configured in many ways with a detector as disclosed herein. The spectrometer may comprise a plurality of optical filters, such as an array of optical filters. A plurality of detectors comprising concentric annular elements can be located at locations corresponding to the filters of the filter array. An array of lenses can be coupled to the array of optical filters and an array of concentric detectors as disclosed herein. The array of concentric detectors may comprise a plurality of concentric detectors as disclosed herein, each having a center element located along an optical axis of the corresponding lens and filter of the lens array and filter array, respectively.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A detector to measure spectra of a sample, comprising:
a plurality of arcuate photo sensor elements; and
circuitry coupled to the plurality of arcuate photo sensor elements to measure an amount of light incident on each of the plurality of arcuate photo sensor elements,
each arcuate photo sensor element of the plurality of arcuate photo sensor elements comprising a radial thickness, wherein a first radial thickness of a first arcuate photo sensor element of the plurality of arcuate sensor elements is larger than a second radial thickness of a second arcuate photo sensor element of the plurality of arcuate sensor elements, wherein the first arcuate sensor element is closer to a common center of the plurality of arcuate photo sensor elements than is the second arcuate sensor element.

2. The detector of claim 1, wherein the plurality of arcuate photo sensor elements comprises a plurality of concentric photo sensor elements.

3. The detector of claim 2, wherein each arcuate photo sensor element of the plurality of arcuate photo sensor elements comprises a circumferential shape profile corresponding to a center of curvature concentric with other arcuate photo sensor elements of the plurality of arcuate photo sensor elements.

4. The detector of claim 1, wherein the plurality of arcuate photo sensor elements comprises a plurality of ring segments.

5. The detector of claim 1, wherein the plurality of arcuate photo sensor elements comprises a plurality of annular elements extending around a central photo sensor element.

6. The detector of claim 1, wherein the plurality of arcuate photo sensor elements comprises a plurality of annular elements, each annular element of the plurality of annular elements extending at least partially around a central circular photo sensor element.

7. The detector of claim 1, wherein the plurality of arcuate photo sensor elements comprises a plurality of annular elements, each annular element of the plurality of annular elements comprising a radial thickness, wherein the radial thickness of the plurality of annular elements decreases progressively for said each annular element away from a common center of the plurality of annular photo sensor elements.

8. The detector of claim 1, wherein the plurality of arcuate photo sensor elements is collectively configured to sense light having a wavelength within a short-wavelength infrared range.

9. The detector of claim 1, wherein the plurality of arcuate photo sensor elements is collectively configured to sense light having a wavelength greater than about 1 µm.

10. The detector of claim 1, wherein each arcuate photo sensor element of the plurality of arcuate photo sensor elements is configured to be measured separately using a separate electrical connection.

11. The detector of claim 1, further comprising a plurality of anode bonds coupling each arcuate photo sensor element of the plurality of arcuate photo sensor elements with the circuitry, and a single common cathode bond coupling the plurality of arcuate photo sensor elements with the circuitry.

12. The detector of claim 1, further comprising a plurality of cathode bonds coupling each arcuate photo sensor element of the plurality of arcuate photo sensor elements with the circuitry, and a single common anode bond coupling the plurality of arcuate photo sensor elements with the circuitry.

13. The detector of claim 1, wherein the plurality of arcuate photo sensor elements define a clearing, and wherein the detector further comprises electrical wires to couple the plurality of arcuate photo sensor elements to the circuitry, the electrical wires coupled to the plurality of the arcuate photo sensor elements at the clearing.

14. The detector of claim 1, wherein each arcuate photo sensor element of the plurality of arcuate photo sensor elements comprises a plurality of segments, each segment of the plurality of segments configured to be measured separately using a separate electrical connection.

15. The detector of claim 1, wherein the plurality of arcuate photo sensor elements comprises one or more of silicon PIN, lattice matched indium gallium arsenide (InGaAs), strained InGaAs, mercury cadmium telluride (MCT), superlattice, lead(II) sulfide (PbS), geranium (Ge), indium antimonide (InSb), lead(II) selenide (PbSe), photovoltaic MCT (PV MCT), indium arsenide (InAs), or other infrared semiconductors.

16. A spectrometer, comprising:
   optics configured to receive input light and generate output light having an arcuate optical pattern; and
   a detector configured to receive the output light having the arcuate optical pattern, the detector comprising a plurality of arcuate photo sensor elements,
   each arcuate photo sensor element of the plurality of arcuate photo sensor elements comprising a radial thickness, wherein a first radial thickness of a first arcuate photo sensor element of the plurality of arcuate sensor elements is larger than a second radial thickness of a second arcuate photo sensor element of the plurality of arcuate sensor elements, wherein the first arcuate sensor element is closer to a common center of the plurality of arcuate photo sensor elements than is the second arcuate sensor element.

17. A method of measuring spectra of input light, the method comprising:
   providing a spectrometer comprising optics and a detector, the detector comprising a plurality of arcuate photo sensor elements shaped to correspond to an arcuate optical pattern of the input light transmitted through the optics;
   measuring an amount of light incident on each of the plurality of arcuate photo sensor elements; and
   determining the spectra of the input light based on measurement data generated by the plurality of arcuate photo sensor elements,
   each arcuate photo sensor element of the plurality of arcuate photo sensor elements comprising a radial thickness, wherein a first radial thickness of a first arcuate photo sensor element of the plurality of arcuate sensor elements is larger than a second radial thickness of a second arcuate photo sensor element of the plurality of arcuate sensor elements, wherein the first arcuate sensor element is closer to a common center of the plurality of arcuate photo sensor elements than is the second arcuate sensor element.

18. The method of claim 17, wherein each of the plurality of arcuate photo sensor elements comprises a plurality of segments, and wherein the measuring comprises measuring an amount of light incident on each segment of the plurality of segments using a separate electrical connection, and summing measurements from the plurality of segments.

19. A method of manufacturing a detector, the method comprising patterning a plurality of arcuate photo sensor elements using photolithography,
   each arcuate photo sensor element of the plurality of arcuate photo sensor elements comprising a radial thickness, wherein a first radial thickness of a first arcuate photo sensor element of the plurality of arcuate sensor elements is larger than a second radial thickness of a second arcuate photo sensor element of the plurality of arcuate sensor elements, wherein the first arcuate sensor element is closer to a common center of the plurality of arcuate photo sensor elements than is the second arcuate sensor element.

* * * * *